US010989571B2

(12) United States Patent
Hunziker et al.

(10) Patent No.: US 10,989,571 B2
(45) Date of Patent: Apr. 27, 2021

(54) SENSOR PACKAGE

(71) Applicant: SENSIRION AG, Stäfa (CH)

(72) Inventors: Werner Hunziker, Stäfa (CH); David Pustan, Stäfa (CH); Matthias Boeller, Stäfa (CH); Stephan Braun, Stäfa (CH)

(73) Assignee: SENSIRION AG, Stafa (CH)

( * ) Notice: Subject to any disclaimer, the term of this patent is extended or adjusted under 35 U.S.C. 154(b) by 0 days.

(21) Appl. No.: 16/608,948

(22) PCT Filed: Apr. 24, 2018

(86) PCT No.: PCT/EP2018/060467
§ 371 (c)(1),
(2) Date: Oct. 28, 2019

(87) PCT Pub. No.: WO2018/197484
PCT Pub. Date: Nov. 1, 2018

(65) Prior Publication Data
US 2020/0182661 A1    Jun. 11, 2020

(30) Foreign Application Priority Data

Apr. 28, 2017 (EP) ..................................... 17168692

(51) Int. Cl.
*G01D 11/24* (2006.01)
*G01N 33/00* (2006.01)

(52) U.S. Cl.
CPC ....... *G01D 11/245* (2013.01); *G01N 33/0036* (2013.01)

(58) Field of Classification Search
CPC ... G01D 11/245; G01D 11/24; G01N 33/0036
See application file for complete search history.

(56) References Cited

U.S. PATENT DOCUMENTS 5,207,102 A * 5/1993 Takahashi ............. G01L 19/147
73/727
6,266,197 B1 * 7/2001 Glenn ..................... G01J 5/045
359/819
(Continued)

FOREIGN PATENT DOCUMENTS

EP       2 952 886 A1    12/2015
EP       2952886 A1  *  12/2015 ........... G01D 11/245

OTHER PUBLICATIONS

ISR for International Application PCT/EP2018/060467.
Written Opinion for International Application PCT/EP2018/060467.

*Primary Examiner* — Jamel E Williams
(74) *Attorney, Agent, or Firm* — Ladas & Parry LLP

(57) ABSTRACT

A sensor package comprises a sensor chip (3) with a sensitive element (31) exposed to an environment of the sensor package, and contact pads (2) for electrically contacting the sensor package. Electrical connections (5) are applied between the sensor chip (3) and the contact pads (2). A molding compound (1) at least partially encloses the sensor chip (3) and the contact pads (2). A unit (3, 73) consisting of the sensor chip (3) and optionally of a die pad (73) supporting the sensor chip (3) is arranged such that a top surface (ts) of the unit (3, 73) does not protrude from a level defined by a top surface (ts) of the contact pads (2), and a bottom surface (bs) of the unit (3,73) does not protrude from a level defined by a bottom surface (bs) of the contact pads (2).

18 Claims, 4 Drawing Sheets

(56) References Cited

U.S. PATENT DOCUMENTS

| | | | | |
|---|---|---|---|---|
| 6,492,699 | B1* | 12/2002 | Glenn | H01L 27/14618 257/433 |
| 6,624,921 | B1* | 9/2003 | Glenn | B81B 7/0067 257/680 |
| 6,629,633 | B1* | 10/2003 | Glenn | H01L 27/14618 228/175 |
| 6,667,543 | B1* | 12/2003 | Chow | H01L 21/565 257/434 |
| 6,958,261 | B2* | 10/2005 | Chow | H01L 21/565 257/673 |
| 8,008,762 | B2* | 8/2011 | Bolken | H01L 24/97 257/680 |
| 10,225,635 | B2* | 3/2019 | Brioschi | H04R 1/04 |
| 2005/0186703 | A1* | 8/2005 | Weiblen | B81B 7/0051 438/106 |
| 2007/0263367 | A1 | 11/2007 | Fischer et al. | |
| 2008/0009102 | A1* | 1/2008 | Yang | H01L 21/568 438/126 |
| 2008/0017956 | A1 | 1/2008 | Lu et al. | |
| 2008/0157236 | A1* | 7/2008 | Chen | G01L 19/141 257/415 |
| 2008/0191333 | A1* | 8/2008 | Yang | H01L 27/14618 257/680 |
| 2008/0246133 | A1 | 10/2008 | Derderian | |
| 2009/0155956 | A1 | 6/2009 | Pohl et al. | |
| 2009/0230487 | A1* | 9/2009 | Saitoh | B81C 1/00333 257/419 |
| 2010/0164082 | A1* | 7/2010 | Fujisawa | H01L 27/14618 257/680 |
| 2013/0001761 | A1* | 1/2013 | Rogren | H01L 23/49582 257/676 |
| 2015/0090030 | A1* | 4/2015 | Theuss | H01L 21/52 73/431 |
| 2015/0219513 | A1* | 8/2015 | Uematsu | G01L 9/0052 73/754 |

\* cited by examiner

SENSOR PACKAGE

FIELD OF THE INVENTION

The present invention relates to a sensor package and to a method for manufacturing a sensor package.

TECHNICAL BACKGROUND

An increasing number of sensors tend to be integrated into semiconductor chips. Such sensor chips may be packaged. The resulting sensor package may be used as a component of an electronic device, and, for example, be arranged within a housing of such device. It is desired to reduce a volume of sensor packages, in particular in view of a reduced space those sensor packages are allowed to claim within an electronic device.

EP2952886 (A1) is directed to methods for manufacturing a gas sensor package, as well as a gas sensor package manufactured according to such methods. The method comprises the steps of mounting a semiconductor chip on a carrier and applying a molding compound for at least partially enclosing the semiconductor chip thereby generating an opening in the molding compound. The opening provides access to a portion of the semiconductor chip being uncovered by the molding compound. A sensitive material is applied through the opening onto the uncovered portion of the semiconductor chip for building a layer sensitive to a gas. It is preferred that the opening in the molding compound is arranged in a front side of the gas sensor package while contact pads and a die pad are arranged at a back side thereof. For example, the gas sensor package may have the shape of a cuboid which is defined by a molding compound and which has a front side and a back side opposite to the front side. An opening in the molding compound provides access to a sensitive layer of a gas sensor chip. In side walls, front ends of contact pads are exposed from the molding compound as well as front ends of support leads. The back side of the gas sensor package shows six contact pads. The contact pads are arranged in two rows of three contact pads each at two opposite edges of the gas sensor package.

DISCLOSURE OF THE INVENTION

Hence, according to a first aspect of the invention, a sensor package is provided comprising a sensor chip including a sensitive element.

The sensitive element is sensitive to a measurand, such as gas, humidity, pressure, flow, or others, and preferably to an environmental measurand, i.e. a measurand in the environment of the sensor package or a corresponding electronic device. The material the sensitive element is made of nay include metal oxide e.g. for gas sensing, a polymer for humidity sensing, or others. In order to enable measuring such environmental measurand, the sensitive element is exposed from the sensor package and is granted access to the environment.

The sensor chip, also referred to as die, may contain a semiconductor substrate, such as a silicon substrate, into which circuitry may be integrated. Layers, such as CMOS layers may be provided on top of the substrate for contributing to the integrated circuitry and for contacting the sensitive element. The sensor chip preferably has a top surface and a bottom surface, wherein in one embodiment the sensitive element is arranged on or in the top surface. The sensitive element may be arranged on top of the semiconductor substrate or on top of a layer, such as one of the CMOS layers. In case circuitry is integrated in the sensor chip, the sensitive element may be connected thereto for pre-processing signals from the sensitive element in the circuitry. In a preferred embodiment, the sensor chip comprises terminals, preferably exposed from its top surface. A terminal serves for electrically contacting the sensor chip.

The sensor package comprises contact pads for electrically contacting the sensor package. The contact pads are electrically connected to the terminals of the sensor chip, which electrical connections may be embodied as bond wires or electrically conducting layers such as printed conducting paths. The contact pads are made from electrically conducting material. Hence, each contact pad is represented by an individual electrically conducting element electrically isolated from the other contact pads. The number of contact pads depends on the application and other requirements of the sensor package. The contact pads are preferably arranged around the sensor chip, or, in other words, the sensor chip is arranged in the center of the contact pads in a common plane. Accordingly, it is preferred that the contact pads face side faces of the sensor chip which side faces of the sensor chip are defined as faces connecting its top surface with its bottom surface.

It is preferred, that each contact pad at least partly is exposed to the environment and as such is accessible from the outside. In case the contact pads are exposed from a bottom surface of the sensor package, the sensor package can be SMD mounted to a carrier. In another embodiment, each contact pad is exposed from the bottom surface as well as from the top surface. Its top surface may then even allow for stacking of multiple packages (sensor or IC), flip-chip soldering on, or wire bonding to a carrier. In addition, a side face of each contact pad may be exposed from the sensor package. This may allow for an optical inspection of an SMD mounted sensor package when solder material is applied between the bottom surface of the contact pads and corresponding pads of the carrier.

A molding compound is applied and partly encapsulates the sensor chip and the contact pads. The molding compound preferably is a plastic material, and in a very preferred embodiment is an epoxy with filler particles which filler particles e.g. may be glass. The molding compound may be applied in a molding step, such as by injection-molding or transfer-molding. A hardening step may be applied thereafter if required. Preferably, the molding compound not only serves as partial encapsulation of the sensor chip and the contact pads and hence as protection, but also serves as mechanical support holding and fixing the sensor chip and the contact pads. In some embodiments, an access opening is provided in the molding compound for allowing the medium to be measured to access the sensitive element.

The sensor chip typically has a footprint defined by its length and its width, and has a height. The height is defined as a distance between the top surface and the bottom surface of the sensor chip. Typically, above mentioned CMOS layers define the top surface of the sensor chip. Each contact pad has a height, too, in the same vertical orientation as the sensor chip. In case a contact pad has portions of different height, a maximum height of the portions of the contact pad shall define the height of the contact pad/s for the following purposes. Preferably, the contact pads all have the same height. However, in case of contact pads of different height, the minimum height of a contact pad of such set is defined as the height of the contact pads. Each contact pad has a top surface and a bottom surface in parallel to the top surface and the bottom surface of the sensor chip. According to the above height definitions, the top surface of a single contact pad with portions of different heights is defined as the top surface of the highest portion of such contact pad. In case of contact pads of different heights, the top surface of the contact pads is considered the top surface of the contact pad with the minimum height amongst the contact pads.

In the following, the term "unit" is introduced: The unit may consist of the sensor chip. Accordingly, the top surface and the bottom surface of such unit are identical to the top surface and the bottom surface respectively of the sensor chip, and a height of the unit is equal to the height of the sensor chip. In case the sensitive element is applied onto the top surface of the sensor chip, still the top surface of the sensor chip is considered as top surface of the unit in view of the negligible contribution of the height of the sensitive element, e.g. in form of a thin layer, with respect to the height of the sensor chip.

In a different variant, the unit consists of the sensor chip and a die pad that supports the sensor chip. In this instance, a top surface of the unit typically is identical to the top surface of the sensor chip, but a bottom surface of the unit is represented by a bottom surface of the die pad (assuming that the bottom surface of the sensor chip is attached to and faces a top surface of the die pad). In some examples, the die pad may comprise an opening for granting access to the sensor chip, and in particular a sensitive element of the sensor chip, through such opening. Accordingly, a height of the unit defined as distance between its top and bottom surface exceeds the height of the sensor chip in this instance, and represents a combination of the height of the sensor chip and a height of the die pad, while an attachment layer such as an adhesive between the sensor chip and the die pad may be neglected due to its small contribution to the units height.

The above defined unit has a plane extension that generally extends parallel to each of the top surface and the bottom surface of the unit. This unit is arranged in the sensor package with respect to the contact pads such that the top surface of the unit does not protrude from a level defined by the top surface of the contact pads. Accordingly, in a side view or a side cut, the top of the unit does not exceed the top of the contact pads. The same is true for the bottom surfaces: The bottom surface of the unit does not protrude from a level defined by a bottom surface of the contact pads. Protruding with respect to the bottom surface means, that that the unit does not bulge out from the level defined by the bottom surface of the contact pads. Accordingly, in absolute orientations, the (negated) protrusion with respect to the top surface of the contact pads is defined in plus z-direction, whereas the (negated) protrusion with respect to the bottom surface of the contact pads is defined in minus z-direction.

Accordingly, the vertical extension of the above defined unit is limited by the levels defined by the top and the bottom surface of the contact pads.

Accordingly, in case of lack of a die pad, the height of the sensor chip is equal to or is less than the height of the contact pads while at the same time the sensor chip is (vertically) arranged within the levels defined by the top and bottom surface of the contact pads. Given that contact pads, when made from a leadframe as explained below, are of rather low height e.g. less than 0.5 mm, and preferably in a range between 0.1 mm and 0.4 mm which is the height of the leadframe, it is required that the sensor chip is rather thin. Such thinness may, for example, be achieved by thinning or grinding the original thickness of a wafer or substrate the sensor chip is made from, preferably after having applied circuitry—if any—and/or the sensitive element.

In the event of a die pad, preferably made from the same leadframe the contact pads are made from, and under the assumption that a height of the die pad is less than the height of the contact pads—which implies that the die pad is thinned, e.g. etched, with respect to the contact pads when made from a common leadframe—the combined height of the sensor chip and the die pad, i.e. the height of the unit, is equal to or is less than the height of the contact pads. At the same time, the sensor chip is (vertically) arranged within the levels defined by the top and bottom surface of the contact pads.

Accordingly, the sensor package allows for an integrated, compact and cost effective approach of a molded sensor chip which needs an exposure to the environment for sensing.

In a preferred embodiment, the contact pads are made from a leadframe. The contact pads may represent electrically conducting platforms or leads electrically isolated from each other. In a very preferred embodiment, each contact pad has a landing for the assigned electrical connection at a height less than the height of the contact pad. Preferably, the landings face the side faces of the sensor chip. By such means, a bond wire as electrical connection between a terminal of the sensor chip and the landing of the contact pad can even fully be embedded in the molding compound without the molding compound exceeding the height of the contact pad. Accordingly, a very flat sensor package is provided.

In case the sensor chip has terminals arranged on its top surface the bond wires may be established from each terminal to the assigned contact pad, either onto its landing as described above, or onto the top surface of the contact pad. The first alternative is preferred in case the height of the sensor chip is less compared to the height of the contact pads, and preferably is less than two thirds of the height of the contact pads, in order to build a flat sensor package. The second alternative is preferred in case the sensor chip is of equal height to the contact pads, or only little less e.g. by maximum a third less. In the second alternative, the height of the sensor package may exceed the height of each of the sensor chip and the contact pads owing to a protruding molding compound which may be required to embed the boding wires and to at least partially enclose the contact pads and the sensor chip for mechanical support purposes. In any of the alternatives, it is preferred that the molding compound at least fills a space between the contact pads and the sensor chip and embeds the electrical connections.

In case the sensitive element is arranged on or in the top surface of the sensor chip, it is preferred that an access opening is provided in the molding compound for exposing the sensitive element to the environment of the sensor package. In such case, it is preferred that a frame is arranged on the top surface of the sensor chip which frame encircles the sensitive element, thereby defining the access opening. In one embodiment, a combined height of the unit and the frame is less than the height of the contact pads. In a different embodiment, a combined height of the unit and the frame is equal to the height of the contact pads and represents a height of the sensor package. In particular if the combined height of the sensor chip and the frame is equal to the height of the contact pads, the frame and the contact pads may serve as a support for an upper mold during molding. Hence, the upper mold can even be flat and directly sit on the frame and the contact pads during molding.

The frame may either be bonded to the sensor chip or be manufactured in photolithographic steps. It preferably acts as a barrier preventing the molding compound from entering the area designated for the sensitive element or from covering the sensitive element if already arranged on the sensor chip.

The frame may not necessarily be removed after molding but preferably becomes part of the sensor package and continues to define the access opening in the molding compound. The frame preferably is of a material different than the molding compound. Accordingly, the frame serves the purpose for separating the sensitive element from the molding compound during and after molding.

In a different approach for manufacturing the molding compound and the access opening, an upper mold used in the molding process may have a protrusion. In this case, the sensor area may be protected from mechanical impact during molding and the area for the designated sensitive element may be sealed by a preferably elastic layer arranged on the upper mold or on top of the sensor chip. After molding, the elastic layer may be removed again.

Preferably, the bottom surface of the sensor chip is exposed from the molding material, and is also exposed from the sensor package, while the sensitive element is exposed from the top surface of the sensor chip in case the sensitive element is provided at its top surface. Here, the leadframe and hence the sensor package lacks of a die pad to arranged the sensor chip on. In a different embodiment, a die pad may still be provided and, e.g. manufactured from the same leadframe. The die pad serves as support for the sensor chip, i.e. the sensor chip is arranged on the die pad with its bottom surface facing the die pad. In such embodiment, it is preferred that the die pad is thinned compared to the contact pads, and hence, thinned, e.g. etched, with respect to the original thickness of the leadframe. In this embodiment, the bottom surface of the sensor chip is not exposed, but the bottom surface of the die pad is.

In a different embodiment, the sensitive element is arranged on or in the bottom surface of the sensor chip which preferably is exposed. The terminals, and circuitry if any may remain at the top surface of the sensor chip, and may be electrically connected to the sensitive element by way of through vias leading through the substrate of the sensor chip. In this embodiment, access is granted to the sensitive element from the bottom of the sensor package. In case the bottom surface of the sensor chip is exposed, no specific access opening is required in the molding compound. The molding compound may fill the space between the contact pads and the sensor chip, and may also cover the top surface of the sensor chip, in particular when the height of the sensor chip is less than the height of the contact pads. Preferably, no die pad is used.

The sensor chip may contain additional features to support the operation of the sensitive layer, e.g. a suspended membrane to achieve thermal insulation in case this is required for sensing. In such embodiment, the sensitive element may be arranged on or in the membrane. In a preferred embodiment, the membrane is manufactured by etching, such as dry-etching or wet-etching, or otherwise removing material from the bottom surface of the sensor chip, such as bulk substrate material, thereby generating a recess into the sensor chip. The remaining material of the sensor chip above the recess forms a membrane which may be formed by CMOS layers and/or parts of the bulk substrate material. In case the sensitive element is arranged on the membrane and the membrane is manufactured or arranged at the top surface of the sensor chip, the bottom surface of the sensor chip again may be exposed and not face a die pad. In such embodiment, the sensitive element may also be accessed from the bottom surface of the sensor chip and e.g. pressure or gas may reach the membrane and/or the sensitive element also from the bottom of the sensor chip. A permeable membrane may be applied ever the recess built by etching the membrane, for protecting the membrane and/or the sensitive element.

In a different embodiment, such sensor chip may be flipped within the sensor package, such that the membrane and the sensitive element continue to be embodied on or in the top surface of the sensor chip, which top surface, however, now is exposed from back side of the sensor package. Terminals may here be provided at the bottom surface of the sensor chip and remain buried by the molding compound. In such variant, the top surface of the sensor chip aligns with what used to be referred to as bottom surface of the contact pads. It is legitimate to claim in such embodiments, that this surface now is considered as top surface of the contact pads while the opposite side denotes their bottom surface. In other words, the unit is arranged in the sensor package with respect to the contact pads such that a top surface of the unit does not protrude from a level defined by a corresponding surface of the contact pads, and a bottom surface of the unit does not protrude from a level defined by (another) corresponding surface of the contact pads. Or, in different word, the top and bottom surfaces of the contact pads constitute the boundaries in z-direction, for the top and bottom surface of the unit.

In both membrane embodiments, access is granted to the membrane and to the sensitive element from the back side and the front side of the sensor package, which is preferred in case the sensor chip is a pressure sensor with a membrane being deflectable subject to the differential pressure at both sides of the membrane, or in case the sensor is a gas sensor.

Preferably, a conducting layer is applied to the molding compound, which conducting layer specifically at least partly covers a surface of the molding compound, and specifically a portion of the surface next to the access opening. The conducting layer preferably is a metallization or other electrically conducting layer. The metallization is electrically connected to one of the contact pads, which preferably is connected to ground potential. Hence, the metallization represents an electrostatic discharge protection element for protecting the sensor chip and/or the sensitive element from an electrostatic discharge. Any electrostatic discharge is trapped by the metallization and is discharged via the contact pad. The metallization can directly be applied to the molding compound (and the sensor chip, if necessary), and can further be structured as desired e.g. by screen printing or evaporation or sputtering through a shadow mask.

In another manufacturing method, the metallization may possibly be photo-lithographically structured. Yet, direct structuring techniques may be preferred to photolithography in some cases, due to some technical constraints (e.g., where a package is not allowed to enter a cleanroom, dimensional constraints making direct structuring methods more suitable, etc.)

In a further alternative, the metallization is jet printed onto the molding compound and the top surface of the contact pad. In case the molding compound passes over to the top surface of the contact pad in question, i.e. without a step in between, the metallization can be deposited as a uniform layer, e.g. by screen printing and/or photo-lithography. Hence, the metallization is a planar metallization preferably at least across a portion of the molding compound, and across at least a portion of the contact pad. In case of a non-planar transition from the molding compound to the contact pad, or in case of a non-planar top surface of the molding compound, jet printing is preferred. This allows to make use of different mold geometries.

In the embodiment of the invention with the sensitive element being arranged at the bottom surface of the sensor chip, this bottom surface, a bottom surface of the molding compound, and a bottom surface of the contact pads may contribute to a plane onto which the metallization preferably is applied to.

In such embodiment, and irrespective if a metallization is applied, the terminals may be located on the top surface of the sensor chip and may be connected by means of bond wires to e.g. landings of the contacts.

In embodiments, the top surface and/or the bottom surface of the unit is essentially level with the top surface and/or the bottom surface, respectively, of the contact pads. E.g., the contact pads may all have the same height and the height of the unit is equal to the height of the contact pads. The molding compound at least partially encloses the sensor chip and the contact pads, so as to fill a space between the contact pads and the unit. The molding compound further exhibits a flat surface that is parallel to said plane extension. This flat surfaces can be a top surface or a bottom surface of the molding compound. In all cases, this flat surface can be made essentially level with the top surfaces or the bottom surfaces, respectively, of the unit and contact pads. Preferably though, both the top surface and the bottom surface of the molding compound form flat surfaces. As a result, the top and/or bottom surfaces of the contact pads, the molding compound and the sensor unit can be made flush, hence resulting in a shallow structure.

The electrical connections shall then advantageously be realized as conducting layers (e.g., printed conducting paths) that extend partially on said flat surface of the molding compound. This way, electrical connections can be achieved, which have a negligible impact on the thickness of the package. Such conducting layers can for instance be obtained using same techniques as used to obtain the metallization.

Said conducting layers may notably extend (partially) on the top surface or the bottom surface of the chip, so as to contact terminals of the chip, wherein said terminals are, each integrated in the chip and yet have, each, a surface that is flush with the top or bottom surface of the chip. This way, the conducting layers can be patterned so as to reach an area corresponding to the flush terminals and contact the latter, so as to ensure signal and/or electrical communications between the chip and contact pads, with little or no impact on the thickness of the package. This, incidentally, typically allows the fabrication complexity and costs to be reduced, compared to methods involving bond wires.

As evoked earlier, the sensor package may further comprise a metallization, e.g., for protecting the sensor chip and/or the sensitive element from electrostatic discharges. This metallization may for instance partly cover the flat surface of the molding compound and, preferably, the top or bottom surface of the unit (or sensor chip) too. That is, the metallization extends in a plane defined by said flat surface and the top or bottom surfaces of the unit and contact pads. The metallization can advantageously be electrically connected to one of the contact pads via a given one of the conducting layers, which is preferably patterned as an extension of the metallization, so as to form part thereof. This way, a shallow package is achieved, in which electrostatic discharges can be suitably managed.

According to another aspect of the present invention, a method is provided for manufacturing a sensor package. First, a support is provided onto which a leadframe and a sensor chip are arranged. The support may be an adhesive tape or another support for temporarily supporting and manufacturing the sensor package or early stages of the sensor package.

A thickness of the leadframe, an etching process applied to the leadframe, and/or a height of the sensor chip may be chosen upfront to allow a height of a unit consisting of the sensor chip and optionally of a die pad supporting the sensor chip being equal to or less than a height of the contact pads. Preferably, the leadframe is etched not only to provide leads and contact pads connected to the leads as such, but also to provide e.g. landings in one or more contact pads e.g. at an intermediate height of the contact pads.

The sensor chip preferably is prepared to include electronic circuitry if any and the sensitive element. In a different embodiment, the sensitive element may be applied later on, even after having applied the molding compound. The sensor chip is also thinned if required to achieve the desired height.

Such sensor chip in a first variant is placed in an opening of the leadframe on the support. In this variant, the leadframe lacks of a die pad for mounting the sensor chip to. In a second variant, the sensor chip is placed onto a die pad of the leadframe, and preferably is attached thereto, e.g. by a die attach film.

However, in the first variant, the sensor chip may also be placed first, and the leadframe second.

The sensor chip is electrically connected to portions of the leadframe representing contact pads for electrically contacting the sensor package, e.g. by bond wires. Then, the sensor chip is least partially enclosed by a molding compound as are the contact pads.

For this reason, the assembly is arranged into a mold preferably including a top mold and a bottom mold. The mold is designed such that preferably top surfaces and bottom surfaces of the contact pads remain exposed. In case the surface of the sensor chip carrying the sensitive element is at least partly to be overmolded, too, the sensitive element is to be protected during molding. For this reason, the above introduced frame may be applied to the top surface of the sensor chip. A sealing structure also referred to as frame that is applied or attached or manufactured and structured on the surface of the sensor chip, i.e. the top surface or the bottom surface. This step is preferably applied prior to the molding step. Properties of the material of the sealing structure may allow for a proper sealing even with some height tolerances. Here, the mold may sit on the top of the frame thereby in combination with the frame preventing that molding compound floods the sensitive element. Specifically in such embodiment, an access opening is provided in the molding compound, e.g. by means of the frame, which access opening allows access to the sensitive element. In such embodiment, the access opening may be sealed by means of a membrane permeable for the medium to measure, but providing protection from mechanical impact.

After molding, the contact pads, and the die pad if any, are separated from a rest of the leadframe in a step also known as singulation, e.g. by dicing or sawing. Prior to such step, the assembly may be detached from the present support that preferably is an adhesive tape, and may be arranged on a different support suitable for the singulation step, which may be a dicing tape, for example. In such step, the sensor package is separated either from leadframe portions not required in the package, and/or from other sensor packages manufactured together in a batch. Finally the resulting sensor package can be removed from the support or from the different support.

Accordingly, the unit is arranged in the sensor package such that a top surface of the unit does not protrude from a level defined by a top surface of the contact pads, and a bottom surface of the unit does not protrude from a level defined by a bottom surface of the contact pads. Again, this unit has a plane extension that generally extends parallel to each of a top surface and the bottom surface of the unit.

In case of a conductive ESD protection directly applied to at least portions of the surface of the molding compound, such ESD protection preferably directly connects to the ground contact pad. This step preferably is performed after molding but prior to singulation.

As indicated above, the sensitive layer may in one embodiment also be applied to the sensor chip late in the process through the access opening—if any—of the already manufactured molding compound. In this embodiment, the sensitive layer may be applied after the molding step, and preferably before the singulation step. The molding compound provides mechanical stability for the sensor packages when applying the sensitive element, e.g. by ink jet printing since the sensor chips are already fixed within the molding compound.

The present sensor package provides a compact small size package suited for being arranged into electronic devices such as mobile phones, tablet computers, or stationary electronic devices, etc. In view of its small height, only an access opening of small volume is to be provided, if at all. Such volume defined by the access opening may be considered as dead volume for the sensitive element and any outgassing of the molding compound affecting the sensitive element may be reduced in view of the smaller dead volume. This enhances the measurement.

Note, the terminologies "contact pads" and "terminals" are specifically used herein to denote electrical connection points for the package and the sensor chip, respectively, for the sake of distinction. Such terminologies are interchangeably used in the literature. Thus, the terminals of the chip can equivalently be regarded as contact pads and the contact pads of the packages can be seen as terminals. Now, it should be kept in mind that such contact pads and terminals may, in both cases, include any kind of electrical contact, or connection point (this including, e.g., electrical lines, or traces, and plated areas), as suitable to connect the packaged chip and enable electrical/data signals to flow to/from the chip.

Other advantageous embodiments of the sensor package are listed in the dependent claims as well as in the description below.

BRIEF DESCRIPTION OF THE DRAWINGS

Embodiments of the present invention, aspects and advantages will become apparent from the following detailed description thereof. Such description makes reference to the annexed drawings, wherein the figures show.

DETAILED DESCRIPTION OF THE DRAWINGS

Figure 1:
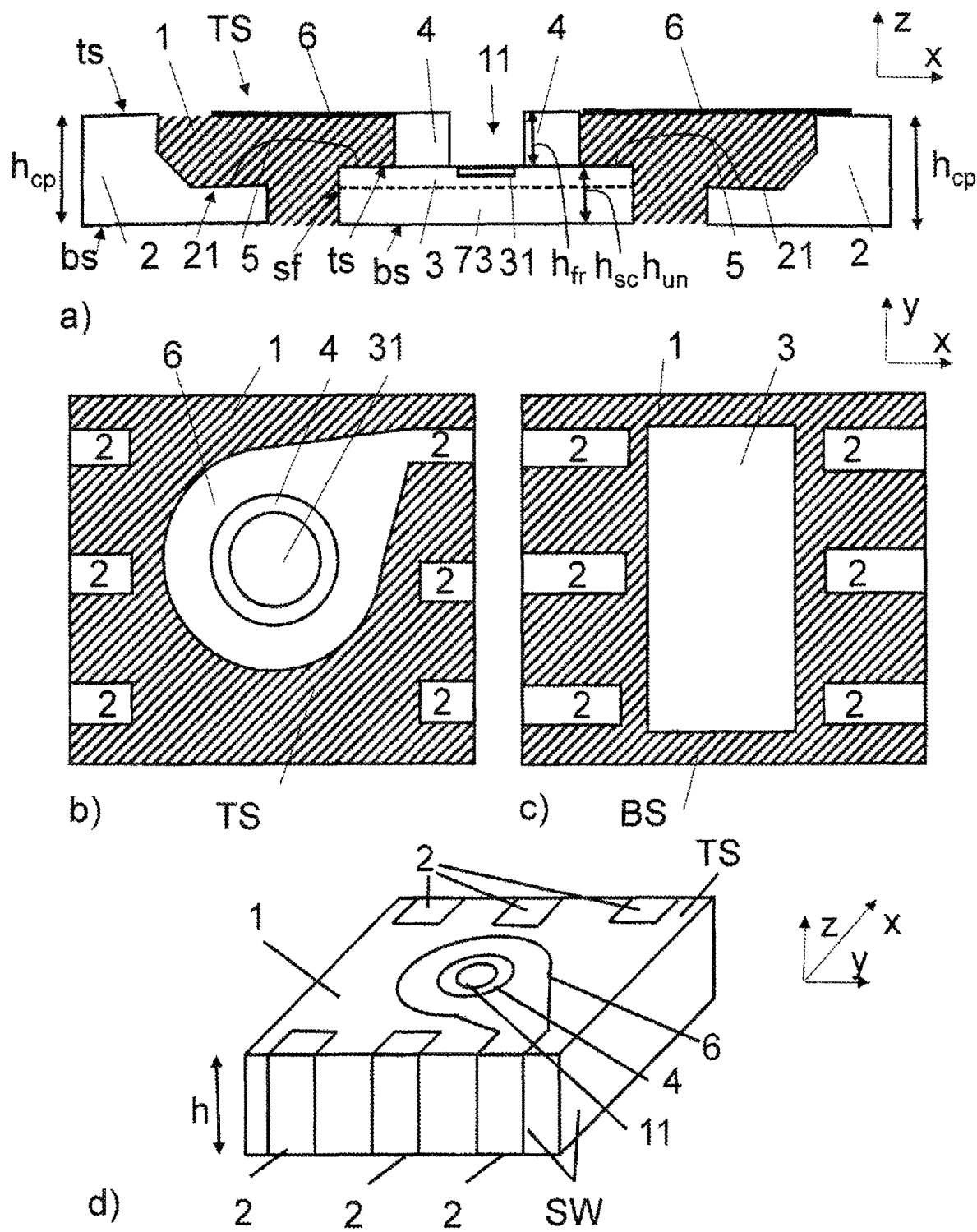
FIG. 1 a sensor package according to an embodiment of the present invention, in a cut view a), in a top view b), in a bottom view c), and in a perspective view d)

Same elements are referred to by the same reference numerals across all Figures.

FIG. 1 illustrates a sensor package according to an embodiment of the present invention. Diagram a) illustrates the sensor package in a cut view, diagram b) in a top view, diagram c) in a bottom view, and diagram d) in a perspective view.

The sensor package has the exemplary shape of a cube with a top side TS and a bottom side BS opposite to the top side TS. A molding compound 1 partly defines the shape of the sensor package. In the present embodiment, the molding compound 1 has a central opening 11 for providing access to a sensitive element 31 of a sensor chip 3.

The sensor chip 3 preferably has a plane extension presently in horizontal x and y direction, and accordingly a top surface ts and a bottom surface bs in parallel to this x-y plane, and a height $h_{sc}$ in vertical z-direction. The sensitive element 31 is arranged on or is integrated in the top surface ts of the sensor chip 3.

Contact pads 2 are provided. The contact pads 2, or at least some of, face side faces sf of the sensor chip 3, which side faces sf are the faces in vertical direction z connecting its top surface ts with its bottom surface bs. The contact pads 2 are represented by individual electrically conducting elements electrically isolated from each other. Each contact pad 2 preferably has a top surface ts, a bottom surface bs, and a height $h_{cp}$. Preferably, the contact pads 2 are manufactured from a leadframe as will be explained in more detail with reference to FIG. 7. The contact pads 2 are made from an electrically conducting material, such as metal, and serve for electrically contacting the sensor package from the outside. Presently, the sensor package includes six contact pads, three at each opposing sides, however, the number and the arrangement may be different from the present example.

In the present embodiment, each contact pad 2 has a landing 21. The landing 21 is considered a platform, which is provided at a height of the contact pad that is less than its overall height $h_{cp}$. The landings 21 face the sensor chip 3, or at least some of the landings 21 do. By doing so, the landings 21 presently serve as landings 21 for electrical connections 5 in form of bond wires. Those bond wires electrically connect to the sensor chip 3, and preferably to terminals of the sensor chip 3 (not shown in FIG. 1).

Presently, no die pad is provided for supporting the sensor chip 3. Accordingly, the unit in the center of the sensor package consists of the sensor chip 3 only, such that the top surface and the bottom surface of the sensor chip correspond to the top surface and the bottom surface respectively of the unit, and such that the height $h_{sc}$ of the sensor chip 3 is identical to a height $h_{un}$ of the unit. Hence, the height $h_{un}$ of the unit 3 is less than the height $h_{cp}$ of the contact pads 2. Specifically, the top surface ts of the unit 3 does not protrude from a level defined by the top surface ts of the contact pads 2, or in other words, does not exceed the level of the top surface ts of the contact pads 2 in +z-direction. At the same time, the bottom surface bs of the unit 3 does not protrude from a level defined by the bottom surface bs of the contact pads 2, or in other words, does not fall below the level of the top surface ts of the contact pads 2 in −z-direction The landings 21 presently are arranged at a level approximately corresponding to the level of the top surface ts of the sensor chip 3. Accordingly, the bond wires can easily be arranged between terminals of the sensor chip 3 and the corresponding contact pads 2 while the bond wires still can be embedded in a molding compound 1.

The molding compound 1 is provided at least in a space between the sensor chip 3 and the contact pads 2 and contributes to the sensor package. Presently, the molding compound 1 provides for a flat sensor package and fills the space between the contact pads 2 and a frame 4 arranged on the top surface ts of the sensor chip 3. The frame 4 represents a protruding structure, e.g. glued or otherwise attached or deposited or grown onto/on the sensor chip 3, and encircles the sensitive element 31. The frame 4 represents an element that during manufacturing prevents the molding compound 1 to cover the sensitive element 31. Hence, it can be considered as a barrier for protecting the sensitive element 31 and preventing the sensitive element 31 to get in touch with the molding compound 1 applied in a liquid or viscous state.

An additional variant is indicated by a dotted line, in which it is assumed that a die pad 73 is provided as a support for the sensor chip 3. In this example, the unit is defined by the combination of the sensor chip 3 and the die pad 73 made from the same leadframe the contact pads 2 are made from. The top surface ts of the unit still is represented by the top surface ts of the sensor chip 3 while the bottom surface bs of the unit now is represented by a bottom surface bs of the die pad 73.

Accordingly, the height $h_{cp}$ of the contact pads 2 is equal to a combined height $h_{un}$ of the unit 3—i.e. the combined height of the sensor chip 3 and the die pad 73—and the one $h_{fr}$ of the frame 4. The molding compound 1 is of the same height, such that the entire sensor package is of height $h_{fr}+h_{un}=h_{op}$. In view of the contact pads 2 preferably being manufactured from a leadframe which typically has a height between 0.1 mm and 0.5 mm, it can be derived that the sensor chip 3 is very thin/flat as is the resulting sensor package. Still, the sensor chip 3 is electrically connected to the contact pads 2 by means of bond wires embedded into the molding compound 1 for protection. The frame 4 defines the access opening 11 in the molding compound 1 ensuring that the medium to be measured reaches to the sensitive element 31.

In a very preferred embodiment the molding compound is at least partly covered by a metallization 6 serving as electrostatic protection element protecting the sensor chip 3 or the sensitive element 31 from electrostatic discharge. In the present example, the metallization 6 is directly deposited onto the molding compound, and preferably encircles the access opening 11. In one embodiment, a top surface of the frame 4 may also be at least partly covered. Any electrostatic discharge trapped by the metallization 6 preferably is discharged via one of the contact pads 2. Presently, the metallization 6 extends on the top surface of the sensor package and specifically of the molding compound 1 towards one of the contact pads 2 and electrically connects thereto. Hence, any electrostatic discharge trapped by the metallization 6 can be discharged via this contact pad 2. In the present embodiment, the metallization 6 is a plane element across the top side TS of the sensor package.

In the present example, solder balls 91 or other electrical contact means as indicated by dotted lines are provided one the bottom surfaces bs of the contact pads 2. Alternatively or in addition, other solder balls 92 or other electrical contact means may be provided on the top surfaces ts of the contact pads 2, e.g. for connecting to another sensor package or IC package stacked on the present sensor package.

In view of the dimensions of the contact pads 2, the sensor chip 3 and the frame 4, the molding process is facilitated. With respect to FIG. 7, the manufacturing of a sensor package is illustrated in more detail. Presently, a support 8 e.g. in form of an adhesive tape is provided. A leadframe 7 is arranged on the support 8, only a portion of which leadframe 7 is presently shown. The leadframe 7 is an electrically conducting structure prepared by etching and provides an opening suitable to place the sensor chip 3 in. At the same time portions of the leadframe 7 serve as contact pads 2. In the present embodiment, the sensor chip 3 is directly placed onto the support 8. However, contact pads 2 are premanufactured in the leadframe 8 in form of extensions extending from leads 71. The sensor chip 3 is placed in the opening/free space between the contact pads 2 onto the support 8. The leadframe 8 and the sensor chip/s 3 may be held in their position on the support 6 by way of adhesion means.

The leadframe 7 may encompass a structure that serves for manufacturing multiple sensor packages from in one batch. Accordingly, although not shown the contact pad 2 structure may repeat to the left, right, top and bottom.

Figure 7:
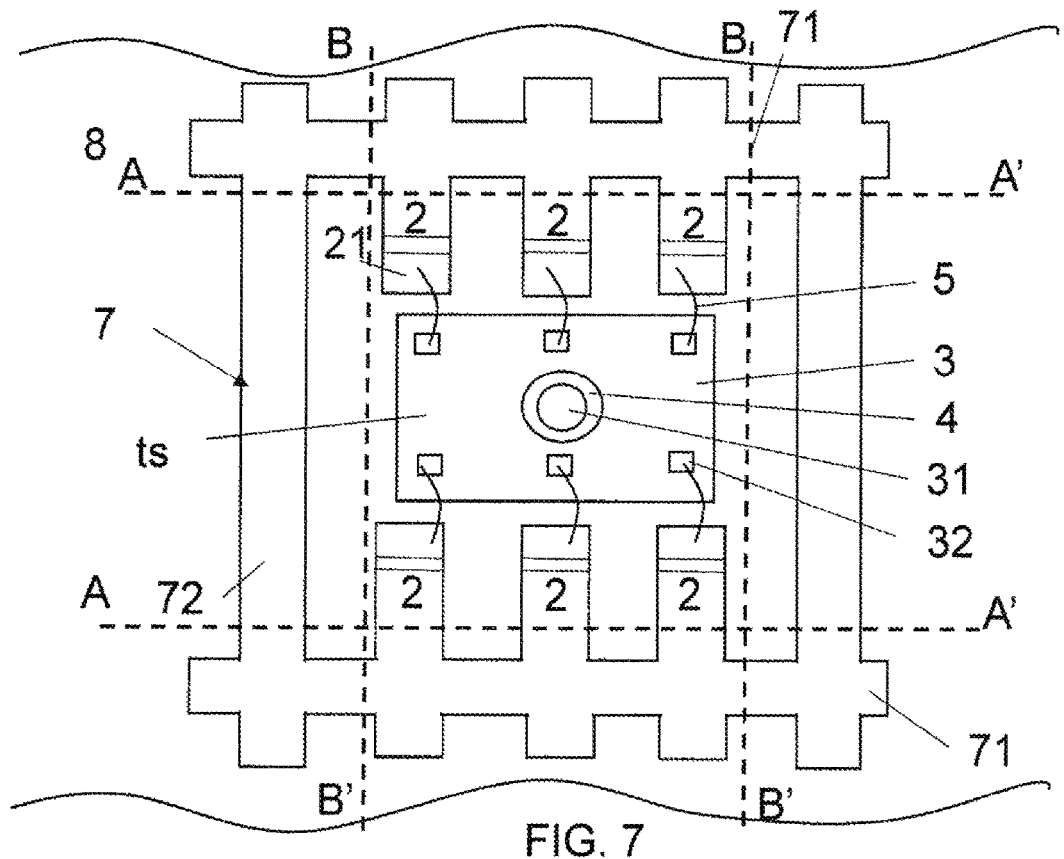
FIG. 7 a top view on an assembly during the manufacturing of a sensor package according to an embodiment of the present invention.

Presently, the sensor chip 3 is arranged on the support 8 with its top surface ts facing away from the support 8, and hence with its bottom surface bs facing the support 8. Accordingly, FIG. 7 illustrates a top view on the top surface ts of the placed sensor chip 3. It is presently assumed that the sensitive element 31 already is manufactured into/onto the top surface ts of the sensor chip 3, as is the frame 4. In addition, terminals 32 are exposed from the top surface ts of the sensor chip 3. The terminals 32 may be manufactured from metallization layers provided on top of a semiconductor substrate of the sensor chip 3 by way of etching, for example.

In a next step, the sensor chip 3 is electrically connected to the leadframe 8. For this reason, electrical connections 5 are provided in from of bond wires. Presently, each terminal 32 is connected to an assigned contact pad 2 by such bond wire. Each of the contact pads 2 has a landing 21 as is illustrated in FIG. 1. Specifically, each bond wire lands on the landing 21 of the assigned contact pad 2. While in one embodiment, it can be assumed that the leadframe 7 has a uniform thickness/height which finally represents the height $h_{sc}$ of the contact pads 2, the landings 21 are provided at a level lower than the top surface of the contact pads and may be achieved by e.g. locally thinning the leadframe 7, such as by way of etching.

In a next step, the molding compound 1 is applied to the assembly shown in FIG. 7. With reference to FIG. 1, it can be derived that the contact pads 2 and the frame 4 on the sensor chip 3 terminate at the same level in z-direction. For this reason, a simple mold can be used for molding such assembly. Such mold may only comprise a bottom mold in form of a plate for placing the assembly including or excluding the support on, and a top mold again in form of a plate resting on the frame/s 4 and the top surfaces ts of the contact pads 2. After having applied the mold to the assembly, the molding compound is filled into the mold and thereby fills the space between the contact pads 2, the sensor chip 3 and the frame 4 respectively. Preferably after hardening, the molding compound 1 provides for a rigid structure partly enclosing the sensor chip 3 and the contact pads 2 and contributing to the sensor package.

However, at this stage, the contact pads 2 are still electrically connected with each other via the corresponding leads 71 and 72. For this reason, after having removed the mold, the assembly is diced in a separating step, e.g. after being transferred from the support 8 to another support such as a dicing tape. For example, the leads 71 and 72 are separated from the contact pads 2 by means of dicing along lines A-A' and B-B', which dicing includes dicing through the molding compound 1 as well. The resulting sensor package may finally be removed from the dicing tape.

Figure 2:
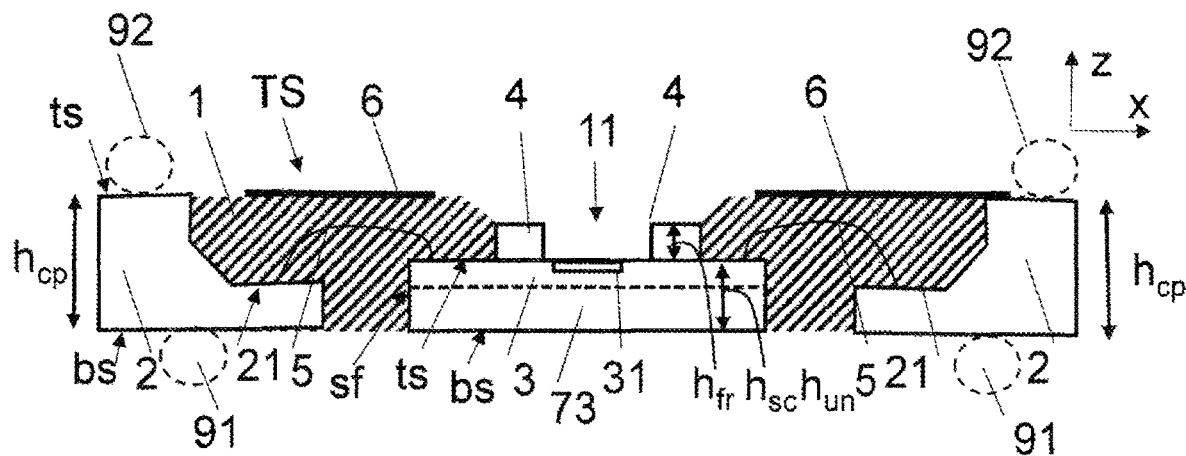
FIGS. 2-6 and 8a), sensor packages according to embodiments of the present invention, in a cut view.

FIG. 2 illustrates another sensor package in a cut view according to an embodiment of the present invention. This embodiment resembles the embodiment of FIG. 1, such that only the differences are addressed in the following: Instead of the frame 4 reaching to a level defined by the top surface ts of the contact pads 2, the height $h_{fr}$ of the frame 4 now is reduced. Accordingly, the mold may provide a protrusion sitting on the top of the frame 4 during molding. The protrusion preferably has a shape as to narrow towards the frame 4 such that a narrowing access opening 11 is generated in the molding compound 1. Again, an additional variant is indicated by dotted lines, in which it is assumed that a die pad 73 is provided as a support of the sensor chip 3. In this example, the unit is defined by the combination of the sensor chip 3 and the die pad 73 made from the same leadframe the contact pads 2 are made from. The top surface ts of the unit still remains represented by the top surface ts of the sensor chip 3 while the bottom surface bs of the unit now is represented by a bottom surface bs of the die pad 73.

The method for manufacturing as explained in connection with FIG. 7 can be applied in the same manner to manufacture the sensor package according to FIG. 2.

Figure 3:
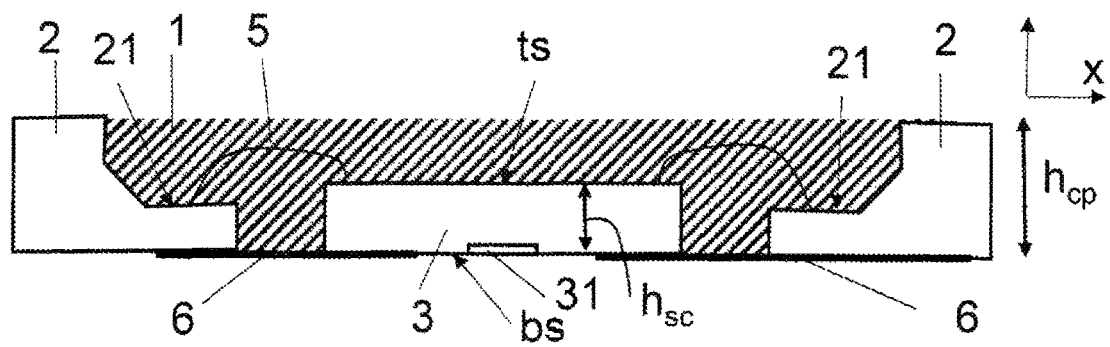

FIG. 3 illustrates a cut view of a sensor package according to another embodiment of the present invention. In contrast to the embodiments of FIG. 1 and FIG. 2, the sensitive element 31 now is arranged on or in the bottom surface bs of the sensor chip 3 instead of its top surface ts. However, its top surface ts still is the face including the terminals for the bond wires as well as circuitry if any. In view of this arrangement of the sensitive element 31, the sensor chip 3 preferably has silicon through vias [not shown]; i.e. electrically conducting paths through the sensor chip 3 from its top surface ts to its bottom surface bs in order to electrically connect the sensitive element 31 to the terminals. Again, the height $h_{sc}$ of the sensor chip 3 representing the height $h_{un}$ of the unit is less than the height $h_{cp}$ of the contact pads 2, and the unit 3 in the center of the contact pads 2 has a top surface ts and a bottom surface bs not protruding from levels defined by the top surface ts and the bottom surface bs of the contact pads 2, i.e. the unit 3 does not exceed these levels in +z and −z-direction respectively.

Again, the contact pads 2 provide landings 21 for the bond wires. In view of the desired embedding of the bond wires into the molding compound 1 and in view of the mechanical stability of the sensor package, the molding compound 1 covers the top surface ts of the sensor chip 3. The bottom surface bs of it remains exposed, however, some portions thereof may be covered by the metallization 6 applied for ESD protection. The metallization 6 again is a plane metallization 6 and covers at least a portion of the bottom surfaces bs the molding compound 1 and the contact pads 2, and possibly the sensor chip 3.

Figure 4:
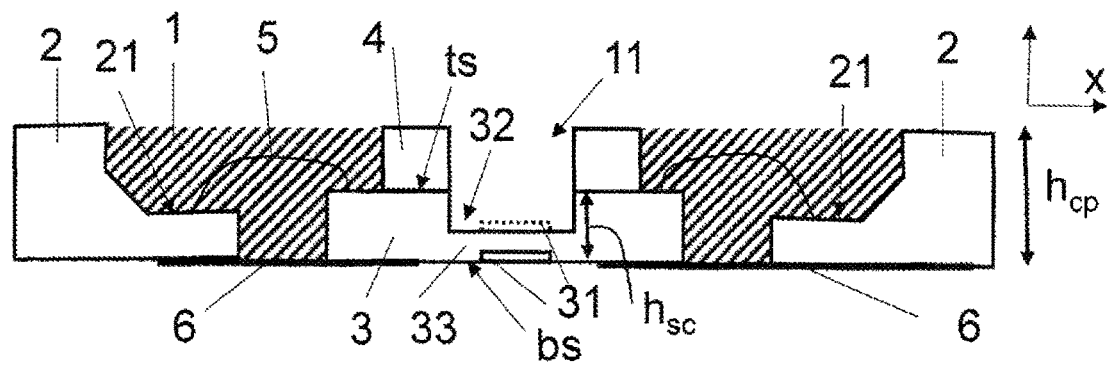

FIG. 4 illustrates another sensor package in a cut view according to an embodiment of the present invention. This embodiment resembles the embodiment of FIG. 3, such that only the differences are addressed in the following: Instead of the top side ts of the sensor chip 3 being completely covered by the molding compound 1, a frame 4 as known from FIGS. 1 and 2 now is arranged on the top side ts, and provides for an opening 11. In addition, a recess 32 is provided in a substrate of the sensor chip 3, and as a result a membrane 33 is built the sensitive element 31 sits on or in. Presently, the sensitive element 31 is arranged at the bottom surface bs of the sensor chip 3 and, hence, the membrane 33, however, as will be appreciated, the sensitive element 31 can also be arranged at the other side of the membrane 33, as indicated by the dotted element 31. In any such embodiment, the membrane 33 is accessible from the front and from the back of the sensor package such that the sensor package in particular qualifies for sensing gas and/or pressure.

Figure 5:
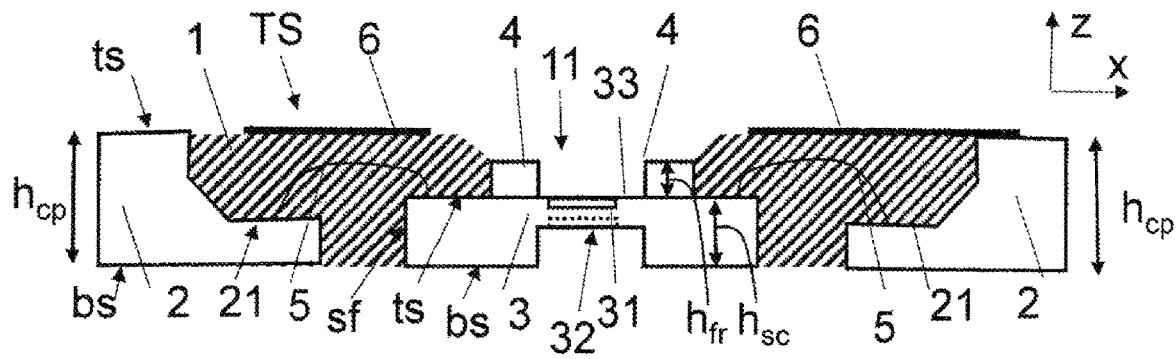

FIG. 5 illustrates another sensor package in a cut view according to an embodiment of the present invention. This embodiment resembles the embodiment of FIG. 2, such that only differences are addressed in the following: A recess 32 is provided in a substrate of the sensor chip 3, and as a result a membrane 33 is built the sensitive element 31 sits on or in. Presently, the sensitive element 31 is arranged at the top surface ts of the sensor chip 3 and, hence, of the membrane 33, however, as will be appreciated, the sensing element 31 can also be arranged at the other side of the membrane 33, as indicated by the dotted element 31. In any such embodiment, the membrane 33 is accessible from the front and from the back of the sensor package such that such sensor package in particular qualifies for sensing gas and/or pressure.

Figure 6:
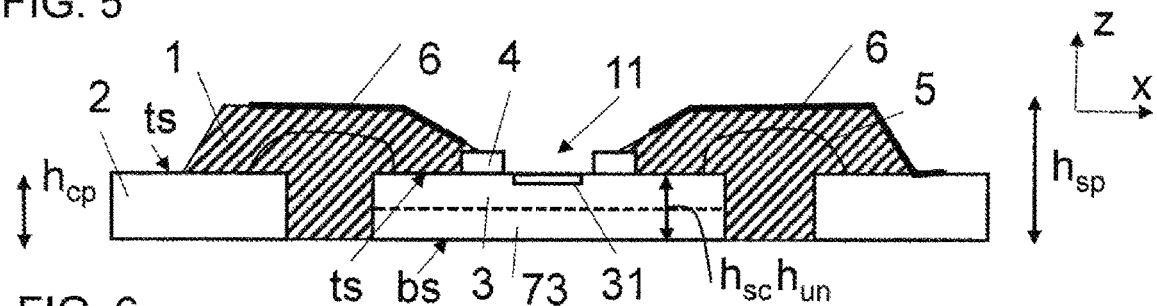

FIG. 6 shows a cut view of a further sensor package according to an embodiment of the present invention. In accordance with the embodiment of FIG. 1, the embodiment of FIG. 6 again has the sensitive element 31 arranged on/in the top surface ts of the sensor chip 3. However, this time the height $h_{sc}$ of the sensor chip 3, i.e. the height of the unit $h_{un}$ in the absence of a die pad, is equal to the height $h_{cp}$ of the contact pads 2. Accordingly, the electrical connections 5 between the terminals of the sensor chip 3 and the contact pads 2 exceed the height $h_{sc}$ anyway, such that in view of a complete embedding of these bond wires the molding compound 1 exceeds this height $h_{sc}$ and provides height $h_{sp}$ as height of the sensor package. Again, a frame 4 is applied to the top surface ts of the sensor chip 3. And a top mold used in the molding process has a shape negative to the resulting molding compound 1. In particular, such top mold has a protrusion sitting on the frame 4 during molding, and further protrusions sitting on the contact pads 2 during molding, such that at least a portion of the top surface ts of the contact pads 2 remains exposed.

FIG. 8a) shows a cross-sectional view of a further sensor package according to an embodiment of the present invention. The plane upon which the view is taken is indicated by a broken line in FIG. 8b). As in FIG. 1, the embodiment of FIG. 8a) again involves a sensitive element 31 arranged on/in the top surface ts of the sensor chip 3. As in FIG. 6, the height $h_{sc}$ of the sensor chip 3 (i.e. corresponding to the height of the unit $h_{un}$ in absence of a die pad) is equal to the height $h_{cp}$ of the contact pads 2, which all have the same height in this example. In variants, however, the contact pads may be portions of the leadframe, as noted earlier.

The molding compound 1 partially encloses the chip 3 and the contact pads 2, so as to fill a space between the contact pads and the unit. However, the molding compound 1 now exhibits top and bottom surfaces that are both flat. Such surfaces are otherwise parallel to the average plane of the unit, which generally has a plane extension. The top and bottom surfaces of the molding compound 1 are essentially level with the top and bottom surfaces (respectively) of both the contact pads 2 and the unit 3, 73.

In variants, though, only one of the top and bottom surfaces of the molding compound 1 can be made flat and level with adjoining surfaces of the contact pads and the unit. Therefore, the top surface and/or the bottom surface of the unit may, more generally, be essentially level with the top surface and/or the bottom surface, respectively, of the contact pads, while the flat surface of the molding compound (i.e., its top or bottom surface) is essentially level with the top or bottom surfaces, respectively, of the unit and contact pads.

Figure 8:
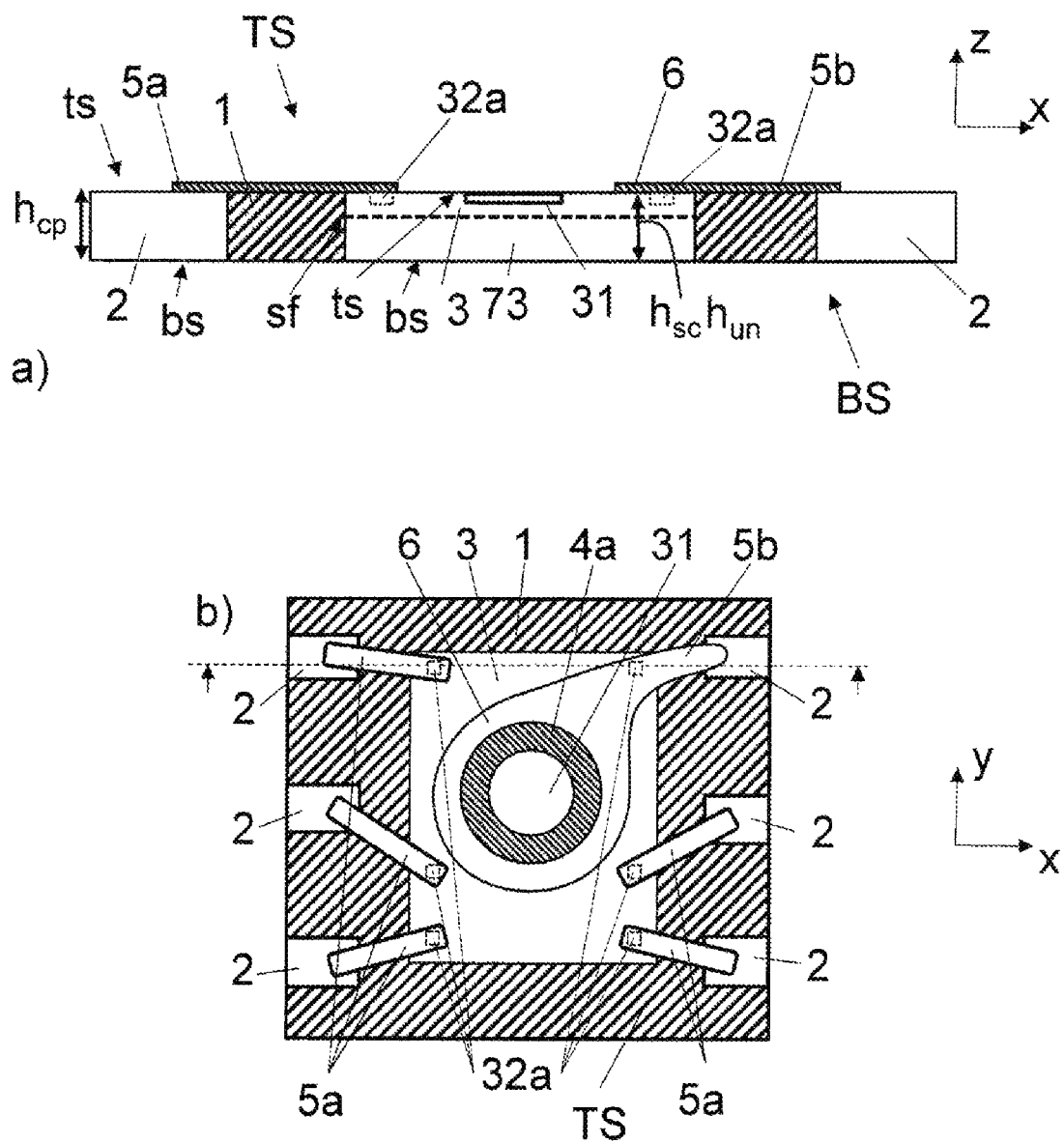
FIG. 8b) a top view of the sensor package of FIG. 8a).

In a flush configuration as shown in FIG. 8, the electrical connections can advantageously be realized as conducting layers 5a, 5b. As better seen in FIG. 8b), such conducting layers 5a, 5b extend partially on the top surface of the molding compound 1, so as to connect the pads 2 to the chip 3. In variants, the conducting layers 5a may similarly extend on the bottom surface of the compound 1 or both the top and bottom surfaces thereof, if needed and appropriate (where any of each of said surfaces is flat), so as to contact terminals of the chip. In the example of FIG. 8, the conducting layers 5a are printed conducting paths. This way, electrical connections can be achieved, which have a negligible impact on the thickness of the package, notwithstanding depictions used in FIG. 8. This, together with the flush configuration of the compound 1, the pads 2 and the unit 3, 73 makes it possible to achieve a particularly shallow package.

As further seen in FIG. 8b), each of the terminals 32a of the chip 3 may be integrated in the chip 3, so as to have a surface that is flush with the top surface of the chip. In turn, the conducting layers 5a, 5b extend, each, partially on the top surface of the chip, so as to contact flush surfaces of the terminals 32a. This way, signals and/or electrical communications can be easily achieved between the chip and contact pads, with little or no impact on the overall thickness of the package. In variants, the chip may include other types of terminals. For example, the chip may already include conductive paths (e.g., traces) printed thereon. In that case, layers 5a, 5b may just need be patterned so as to reach such conductive paths, as necessary to suitably connect the chip.

As further depicted in FIG. 8, the package may further include a metallization 6, for the same reasons as mentioned earlier (ESD protection). The metallization 6 partially covers (i.e., extend on) the top surface of the molding compound 1, as well as the top surface of the chip 3, in this example. The metallization 6 accordingly extends in a plane subtended by the top surfaces of the compounds 1, the contact pads 2 and the unit 3, 73.

As in FIG. 1, the metallization 6 is electrically connected to one of the contact pads 2. In principle, this connection may be achieved thanks to a conducting layer, such as layers 5a, deposited on top of the metallization 6 and the compound 1, so as to connect this pad 2. However, this connection is preferably formed as an extension 5b of the metallization 6 (i.e., so as to form part thereof), as assumed in the example of FIG. 8b). In all cases, both the metallization 6 and conducting layers 5a, 5b may be deposited in a single process step, e.g., using a same printing or deposition through shadow mask process.

Note, the chip 3 may possibly have a membrane configuration, as evoked earlier, just like the chip shown in FIG. 5. In variants, the membrane may be slotted or the chip may have a bridge configuration. Still, it may be realized that, even in such cases, the molding compound 1 can be made level with top and/or bottom planes subtended by the chip and contact pads, while conductive layers 5a, 5b may extend on, e.g., the top surface of the chip, so as to contact flush terminals 32a thereon.

Moreover, a safe area 4a is preferably provided between the sensitive element 31 and the surrounding metallization 6, in order to prevent shorts between the metallization 6 and sensitive element 31. This area 4a may simply consists of a clear area (free of any conducting path) provided on top of the chip 3, so as to form an insulating strip around the sensitive element 31.

Some processing may be required (such as passivation), after metallization 6. In variants, an additional, passivation of electrically insulating material (such as a polymer or an oxide) may deposited on top of the package in order to cover the metallization 6. Other aspects of the fabrication of the package depicted in FIG. 8 may otherwise be essentially similar to those described earlier in reference to FIG. 7.

The invention claimed is:

1. A sensor package, comprising
a sensor chip comprising a sensitive element exposed to an environment of the sensor package,
a unit having a top surface, a bottom surface, and side faces connecting the top surface of the unit with the bottom surface of the unit, wherein the unit consists of either the sensor chip or both the sensor chip and a die pad supporting the sensor chip,
contact pads for electrically contacting the sensor package, wherein each of the contact pads has a top surface and a bottom surface,
electrical connections between the sensor chip and the contact pads, and
a molding compound at least partially enclosing the sensor chip and the contact pads,
wherein,
the unit is arranged in the sensor package with respect to the contact pads such that the top surface of the unit does not protrude from a level defined by a top surface (ts) of the contact pads (2), and the bottom surface of the unit does not protrude from a level defined by a bottom surface (bs) of the contact pads (2), whereby an extension of the unit, as measured along a direction z, is limited by the levels defined by the top surface of the contact pads and the bottom surface of the contact pads, the direction z being orthogonal to each of the top surface and the bottom surface of each of the unit and the contact pads,
and wherein,
each of the contact pads is exposed from both the bottom surface of the contact pads and the top surface of the contact pads, so as to be accessible from an outside of the sensor package.

2. The sensor package of claim 1,
wherein
the contact pads are represented by individual electrically conducting elements electrically isolated from each other,
a height of the unit is equal to or less than a height of the contact pads, and
the direction z is parallel to an orientation defining the height of the contact pads and an orientation defining the height of the unit in the sensor package.

3. The sensor package of claim 1, wherein
each contact pad has a landing for the assigned electrical connection at a level below the top surface of the contact pad and arranged at a side facing a side face of said side faces.

4. The sensor package of claim 1, wherein
the sensitive element is arranged on or in a bottom surface of the sensor chip,
the sensor chip has terminals for the electrical connections at a top surface thereof opposite its bottom surface,
the molding compound at least fills a space between the contact pads and the sensor chip and embeds the electrical connections, and
the bottom surface of the sensor chip exposed.

5. The sensor package of claim 1, wherein
the sensitive element is arranged on or in a top surface of the sensor chip,
the sensor chip has terminals at its top surface for the electrical connections, the molding compound at least fills a space between the contact pads and the sensor chip and embeds the electrical connections.

6. The sensor package of claim 5, further comprising an access opening in the molding compound exposing the sensitive element to the environment of the sensor package.

7. The sensor package of claim 6, further comprising a frame arranged on the top surface of the sensor chip and encircling the sensitive element, thereby defining the access opening.

8. The sensor package of claim 7, wherein a combined height of the unit and the frame as measured along the direction z, is equal to or less than a height of the contact pads as measured along the direction z.

9. The sensor package of claim 7, wherein a combined height of the unit and the frame as measured along the direction z, exceeds the height of the contact pads, and
a height of the sensor package, as measured along the direction z, exceeds a height of the contact pads as measured along the direction z.

10. The sensor package of claim 5, wherein a bottom surface of the sensor chip is exposed from the sensor package.

11. The sensor package of claim 1, wherein the sensor package comprises a metallization at least partly covering a surface of the molding compound, and
the metallization is electrically connected to one of the contact pads.

12. The sensor package of claim 11, wherein the metallization represents an electrostatic discharge protection element for protecting the sensor chip and/or the sensitive element from an electrostatic discharge.

13. The sensor package of claim 11, wherein the metallization contacts said one of the contact pads at its top surface.

14. The sensor package of claim 11, wherein a combined height of the unit and the frame, as measured along the direction z, is equal to or less than a height of the contact pads as measured along the direction z,
the metallization extends in a plane defined by a top surface of the molding compound and the top surface of the contact pads.

15. The sensor package of claim 1, wherein the top surface and/or the bottom surface of the unit is essentially level with the top surface and/or the bottom surface, respectively, of the contact pads,
the molding compound at least partially encloses the sensor chip and the contact pads, so as to fill a space between the contact pads and the unit,
the molding compound has a flat surface parallel to the top surface and the bottom surface of the unit, said flat surface being a top surface or a bottom surface of the molding compound, and is essentially level with the top surfaces or the bottom surfaces, respectively, of the unit and contact pads, and
the electrical connections are conducting layers that extend, each, partially on said flat surface of the molding compound.

16. The sensor package of claim 15, wherein said conducting layers further partially extend on a top surface or a bottom surface of the sensor chip, so as to contact terminals of the chip, wherein said terminals are, each, integrated in the chip and have, each, a surface that is flush with the top surface or the bottom surface of the chip.

17. The sensor package of claim 15, wherein the package further comprises a metallization that partially covers said flat surface of the molding compound whereby the metallization extends in a plane defined by said flat surface, and
the metallization is electrically connected to one of the contact pads via one of said conducting layers.

18. Method for manufacturing a sensor package according to claim 1, the method comprising
providing a support,
arranging a leadframe on the support and the sensor chip on one of the support and a die pad of the leadframe if any,
electrically connecting the sensor chip to portions of the leadframe representing contact pads for electrically contacting the sensor package,
at least partially enclosing the sensor chip and the contact pads by a molding compound,
separating the contact pads from a rest of the leadframe, and
removing the resulting sensor package from the support or a different support, so as to obtain said sensor package.

* * * * *